(12) United States Patent
Fornarelli

(10) Patent No.: US 10,357,063 B1
(45) Date of Patent: Jul. 23, 2019

(54) VAPORIZATION DEVICE CHARGER

(71) Applicant: DB INNOVATION INC., Chicago, IL (US)

(72) Inventor: Thomas Fornarelli, Chicago, IL (US)

(73) Assignee: DB INNOVATION INC., Chicago, IL (US)

( * ) Notice: Subject to any disclaimer, the term of this patent is extended or adjusted under 35 U.S.C. 154(b) by 0 days.

(21) Appl. No.: 16/151,127

(22) Filed: Oct. 3, 2018

(51) Int. Cl.
| | |
|---|---|
| *H01M 10/46* | (2006.01) |
| *A24F 47/00* | (2006.01) |
| *H01M 10/48* | (2006.01) |
| *H02J 7/00* | (2006.01) |

(52) U.S. Cl.
CPC ......... *A24F 47/008* (2013.01); *H01M 10/482* (2013.01); *H01M 10/488* (2013.01); *H02J 7/0026* (2013.01)

(58) Field of Classification Search
CPC ...... H02J 7/0042; H02J 7/355; H05B 1/0252; H05B 1/0244; H05B 3/42; H05B 2203/021
USPC ................. 320/107, 108, 114, 115, 132, 148
See application file for complete search history.

(56) References Cited

U.S. PATENT DOCUMENTS

| | | | | |
|---|---|---|---|---|
| 9,609,893 B2* | 4/2017 | Novak, III | ............ | A24F 47/008 |
| 2012/0013291 A1* | 1/2012 | Lahti | ................... | H02J 7/0044 |
| | | | | 320/107 |
| 2012/0295451 A1* | 11/2012 | Hyun-Jun | .......... | H01R 13/6205 |
| | | | | 439/39 |
| 2016/0031338 A1* | 2/2016 | Penilla | ................ | B60L 11/1824 |
| | | | | 320/109 |
| 2017/0135401 A1* | 5/2017 | Dickens | ................ | A24F 47/008 |
| 2017/0303591 A1* | 10/2017 | Cameron | .............. | A24F 47/008 |
| 2017/0325506 A1* | 11/2017 | Batista | .................. | A24F 47/008 |
| 2018/0042306 A1* | 2/2018 | Atkins | .................. | A61M 15/06 |
| 2018/0085551 A1* | 3/2018 | Krietzman | ............ | A24F 47/008 |

* cited by examiner

*Primary Examiner* — Edward Tso
(74) *Attorney, Agent, or Firm* — Flener IP & Business Law; Zareefa B. Flener

(57) ABSTRACT

A rechargeable vaporization device comprises a body configured to house at least two pens and a first printed circuit board (PCB) operatively connected to a rechargeable battery in a cavity inside the body. Each of the at least two pens comprises a sensor, and a coil disposed within each of a plurality of vaporization chambers. A charger is attached to an end of the battery and comprises a second PCB operatively connected to the battery, where the second PCB determines power requirements of the battery and charges the battery according to the power requirements.

19 Claims, 12 Drawing Sheets

VAPORIZATION DEVICE CHARGER

FIELD OF THE INVENTION

The present invention relates to a charger for a vaporization device. More specifically, the present invention relates to a portable charger for safely and conveniently providing power for charging the batteries of a vaporization device.

BACKGROUND

Vaporization devices typically comprise at least a reservoir for electronic liquid ("e-liquid"), a coil or other heat source for vaporizing the e-liquid, a vaporization chamber, a battery or other power source for powering the coil or heat source, a mouthpiece, and a body or housing for accommodating all of the other components. The e-liquid can be composed of essential oils and other chemicals such as nicotine and/or cannabinoids. A wick acts as a bridge between the e-liquid in the reservoir and the vaporization chamber.

The vaporization device can be rather compact resembling a conventional cigarette. Often these sort of compact vaporization devices are referred to as vaporization pens or commonly vape pens. Portable vape pens are typically cordless and require a charged battery or batteries to function. The battery (or batteries) can be a single use disposable battery but is advantageously a multiple use rechargeable battery. Often, the battery is attached to one or more vape pens and/or elements of a vape pen and is not easily separated therefrom for charging. In other instances, there may be multiple batteries that are not easily separable from the vaporization device yet still require charging. Given the portable nature of vape pens, a battery charger suited for charging the batteries of vape pens is also advantageously portable and can secure the batteries within the charger.

Battery chargers for rechargeable batteries are known, for example, rechargeable batteries can be charged using a wall adapter, a portable charging case, or a USB charger. However, known chargers do not secure the batteries, report data on accommodate the features associated with batteries for vape pens. Therefore, a device is needed that can reliably secure and charge the batteries of vape pens.

SUMMARY OF THE INVENTION

The present invention is related to a device with a plurality of pens, each able to accommodate a tank holding a unique e-liquid for vaporization.

The present invention also relates to a device with a plurality of reservoirs each comprising an e-liquid that cannot easily be mixed with the other for vaporization in a single vaporization at a single coil temperature for a combined vaporization product for inhalation by a user.

The present invention further relates to a device which is disposable.

The present invention even further relates to a device which is rechargeable, and also accommodates removably affixed tanks which can be exchanged as desired with other tanks containing a different e-liquid and components.

The present invention moreover relates to a device which can mix a plurality of e-liquids in a vaporization chamber and vaporize the mixture at one temperature.

The present invention relates to a device which can vaporize an e-liquid and combine the vaporization produce with e-liquid vaporized by a different coil at a different temperature and in a different vaporization chamber, while combining or mixing the plurality of vaporization products produced from each vaporization together in a vapor port for inhalation by the user.

According to one aspect of the invention, a rechargeable vaporization device comprises a body configured to house at least two pens, and a first printed circuit board (PCB) operatively connected to a rechargeable battery in a cavity inside the body. Each pen comprises a sensor and a coil disposed within each of a plurality of vaporization chambers. A charger is attached to an end of the battery and comprises a second PCB operatively connected to the battery, where the second PCB determines power requirements of the battery and charges the battery according to the power requirements.

According to another aspect of the invention, a rechargeable vaporization device comprises a body configured to house at least two pens and a first printed circuit board (PCB) operatively connected to a rechargeable battery in a cavity inside the body. Each pen comprises a sensor and a coil disposed within each of a plurality of vaporization chambers. A plurality of tanks each comprises a reservoir configured to contain an e-liquid, where each reservoir is operatively connected to one of the plurality of vaporization chambers. A charger is attached to an end of the battery and comprises a 10 second PCB operatively connected to the battery, where the second PCB determines power requirements of the battery and charges the battery according to the power requirements.

DETAILED DESCRIPTION

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

Accordingly, the detailed discussion herein of one or more embodiments is not intended, nor is to be construed, to limit the metes and bounds of the patent protection afforded the present invention, in which the scope of patent protection is intended to be defined by the claims and equivalents thereof. Therefore, embodiments not specifically addressed herein, such as adaptations, variations, modifications, and equivalent arrangements, should be and are considered to be implicitly disclosed by the illustrative embodiments and claims described herein and therefore fall within the scope of the present invention.

Further, it should be understood that, although steps of various claimed methods may be shown and described as being in a sequence or temporal order, the steps of any such method are not limited to being carried out in any particular sequence or order, absent an indication otherwise. That is, the claimed method steps are considered capable of being carried out in any sequential combination or permutation order while still falling within the scope of the present invention.

Additionally, it is important to note that each term used herein refers to that which a person skilled in the relevant art would understand such term to mean based on the contextual use of such term herein. To the extent that the meaning of a term used herein, as understood by the person skilled in the relevant art based on the contextual use of such term, differs in any way from any particular dictionary definition of such term, it is intended that the meaning of the term as understood by the person skilled in the relevant art should prevail.

Furthermore, a person skilled in the art of reading claimed inventions should understand that "a" and "an" each generally denotes "at least one," but does not exclude a plurality unless the contextual use dictates otherwise. And that the term "or" denotes "at least one of the items," but does not exclude a plurality of items of the list.

Figure 1:
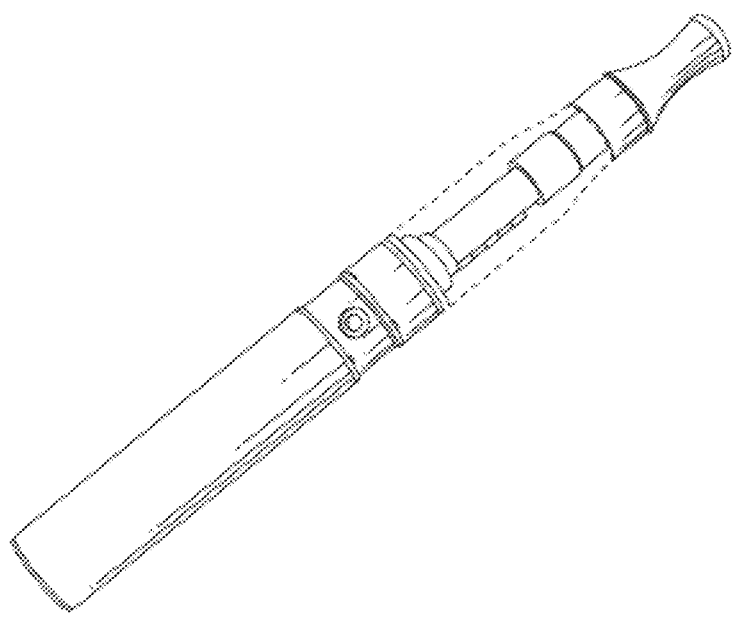
FIG. 1 illustrates a prior art electronic pen or cigarette.

FIG. 1 illustrates an electronic cigarette ("e-cigarette") or electronic pen which is commonly understood and known in the art. Depicted is a front end where the mouthpiece is, adjacent and operatively connected to the tank which contains e-liquid. The tank has a reservoir for e-liquid which is delivered to the coil, which when heated vaporizes the e-liquid. The vaporization process is supported by a sensor recognizing a change in pressure, communicating the same to some sort of printed circuit board or microprocessor which can connect the battery to heat the coil. As is illustrated, e-pens or e-cigarettes deliver vaporized e-liquid to a user through the mouthpiece. The vaporized e-liquid travels through a vapor port up to the mouthpiece and into the user's mouth and lungs.

Figure 2:
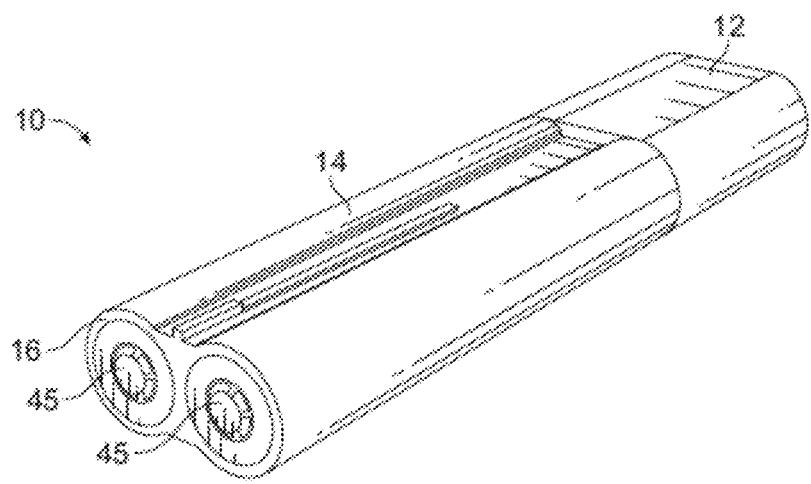
FIG. 2 illustrates an embodiment of the device in accordance with the principles of the present invention.

FIG. 2 illustrates a perspective view of the vaporization device 10 with a first end having a mouthpiece 12 adjacent to a body 14 at a first end of the body, and at a second end of the body 14, the body 14 is adjacent to a ventilated end 16 on a second end of the vaporization device 10 opposing the first end. The ventilated end 16 is provided with a plurality of airflow apertures 45 which can direct air flow through the vaporization device 10. Inside the body 14 of the device 10 is, unlike the pen or e-cigarette shown in FIG. 1, is housed a plurality of pens 18 which each have a battery and either threading compatible with retaining a tank 24 which has a vaporization chamber 26 and a coil 34 therein, or each pen can have a battery 22 plus a vaporization chamber 26 and a coil 34 wherein the vaporization chamber 26 can threadingly receive a tank 24 which has a reservoir containing e-liquid for vaporization (see e.g. FIG. 5). Once the tanks 24 having a vaporization chamber plus coil are appended to the pen battery 22, or tanks 24 appended to a battery 22 having also on the battery a vaporization chamber 26 plus coil 34, the vaporization product produced from a vaporization event travels along a vapor port (not shown) through an aperture 42 (see e.g. FIG. 3) in the mouthpiece 12 to be drawn into a user's mouth and/or lungs. The aperture 42 can be any size that is effective for drawing vapor into the mouth of a user, and the mouthpiece 12 can be any shape and size that is ergonomically suitable for accommodating a plurality of pens 18 and a vapor port through which vaporization products are delivered from the plurality of vaporization chambers 26 in the mouthpiece to the aperture 42.

Figure 3:
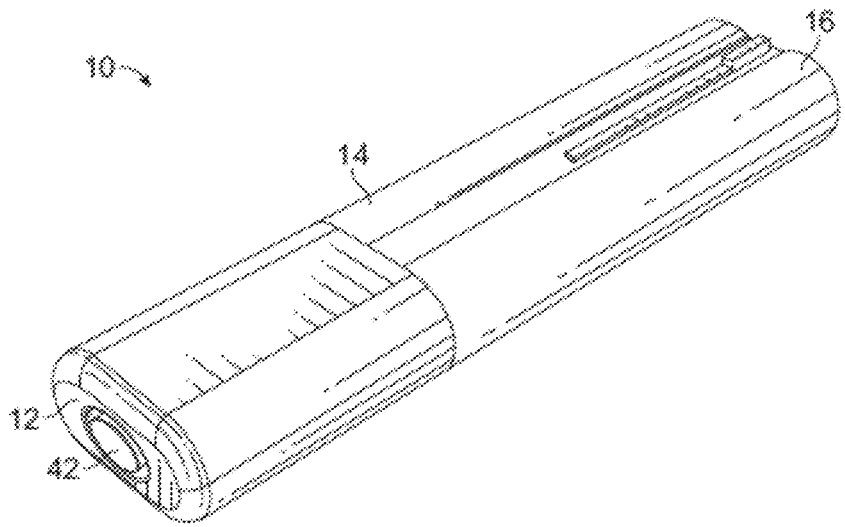
FIG. 3 illustrates an embodiment of the device in accordance with the principles of the present invention.

Preferably, the number of airflow apertures 45 is the same as the number of pens 18 (see e.g. FIGS. 2 and 3 illustrating two pens and two airflow apertures 42) housed in the body 14. This allows for air to flow to each pen through the inside of the device, and also in an embodiment wherein each pen 18 is also provided with its own sensor 20, to direct air flow to each sensor 20 on each pen 18.

FIG. 3 provides another perspective view of the device 10 showing the mouthpiece 12, the body 14, and the ventilated end 16.

Figure 4:
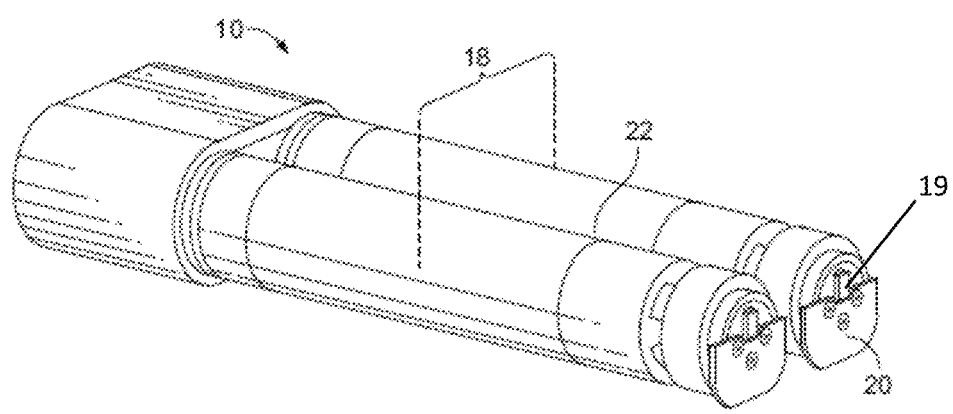
FIG. 4 illustrates an embodiment of the internal components of the body and the ventilated end of the device in accordance with the principles of the present invention.

FIG. 4 illustrates some of the internal components of the vaporization device 10. In this embodiment is shown that the vaporization device 10 is provided with a plurality of pens 18, and in this particular embodiment there are two pens 18. Each pen 18 has its own printed circuit board ("PCB") 19, a sensor 20 for instance, but not limited to, a pressure sensor or an air-flow sensor 20, and a battery 22, which together control the vaporization of e-liquid components in the tank of the pens 18. The PCB may include, for example, but is not limited to, a processing unit, a memory unit, a plurality of timers, and other suitable electrical components. Electronic components of the pen 18 are fixed to the PCB, which mechanically supports and electrically connects components of the assembly using tracks, pads, and other features etched from conductive sheets laminated onto a non-conductive substrate. In some embodiments, the electronics of the PCB is composed of a synthetic material that is thin and flexible. A thin and flexible PCB allows the same to conform to the shape of the electronic cigarette. A PCB is composed of materials such as, but not limited to, polyimide, polyethylene naphthalate, poletherimide, fluoropolymers, transparent conductive polyester, and other suitable materials for flexible electronics.

Figure 5:
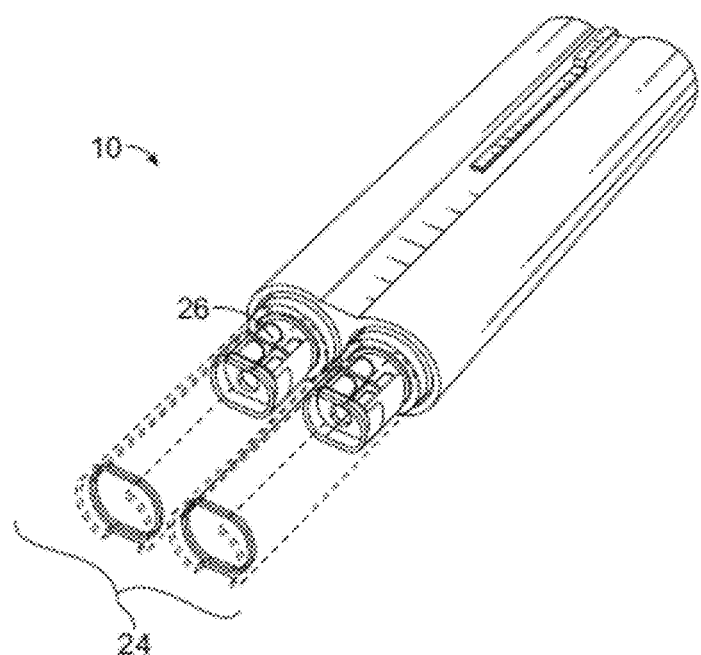
FIG. 5 illustrates an embodiment of the device in accordance with the principles of the present invention.

FIG. 5 illustrates the mouthpiece end of the vaporization device 10. In this particular embodiment, illustrated are two tanks 24 in which e-liquid is received in the reservoirs 28 (see e.g. FIG. 9) of each of the tanks 24. In this embodiment, each tank 24 is attached to a vaporization chamber 26 of each single pen 18. In this way, for each pen 18, a chamber 26 may vaporize a different e-liquid composition, be it an essential oil and/or nicotine and/or different strains of *cannabis* and/or different consistencies and percentages of PG, VG, and water, and can vaporize at a unique temperature apart from another pen of the plurality. This is accomplished by each pen 18 of the plurality of pens being provided with a PCB, battery 22, and sensor 20 to specifically control the temperature and timing of vaporization of the e-liquid in the tank 24 of each pen 18 so as to most closely achieve an ideal vaporization temperature for the molecules in the e-liquid. The vaporization product from each of the vaporization chambers 26 can be mixed in a vapor port for inhalation through the aperture 42 in the mouthpiece 12 of the device 10.

The battery 22 of the device 10 can be rechargeable, can be recharged/charged via induction charging, and/or can be charged by a wall electrical outlet, and/or by accommodating a USB to a computer to recharge/charge. In some embodiments, the battery 22 is a lithium battery, a lithium-ion battery, a nickel-cadmium ("NiCd") battery, a nickel-metal hydride ("NiMH") battery, or another suitable battery type. The battery 22 of each of the pens 18 will be of suitable shape and length to essentially provide the look and feel of an electronic cigarette. In the case of a rechargeable embodiment of the device 10, it is possible for a rechargeable device 10 to be provided with LED lights such that a pattern for charging is detected on the body 14 or the end 16. For example, but not limited to, a pattern whereby lights flash in a pattern when the vaporization device 10 is being charged, and a different pattern when finished.

When the battery is operationally affixed to the tank 24, and the user inhales, each of the pen sensors 20 communicates with the PCB and battery in order that the e-liquid in each of the tanks 24 is vaporized in the chamber 26 producing a vaporization product specific to the e-liquid which has been vaporized at the specific temperature dictated by the PCB of the particular pen 18. Thereafter, the vaporization product from each of the plurality of pens 18 and thus e-liquids is mixed in the vapor port and inhaled through a single mouthpiece 12. In this way, the pleasure of a plurality of different e-liquid vaporization products can be attained in a single vaporization event and at a more effective temperature for each of the plurality of electronic cigarettes 18. This prevents over-heating, creating toxins and bad tastes, and allows for the most accurate and beneficial vaporization of targeted chemicals in each e-liquid, and the e-liquid itself considering PG, VG, and mixes thereof, require different vaporization temperatures. In fact, by providing different vaporization temperatures across each of a plurality of pens 18, a VG heavy e-liquid needing to be vaporized at a higher temperature can be filled in a tank 24 which does not have a cotton wick, and paired with a tank carrying an e-liquid requiring a lower temperature and using a cotton wick, which is not recommended for vaporizing e-liquid which has high VG content. In this way, VG based e-liquid can be vaporized at a high temperature, without evaporating water while burning a cotton wick creating toxins, while at the same time vaporizing a different e-liquid requiring a lower temperature for producing a beneficial vaporization product.

In a disposable embodiment of the device 10, upon the final vaporization of the e-liquid in the reservoir the mouthpiece 12 can be immovably affixed to the body 14. In such an embodiment, the battery 22 need not be rechargeable, and the device in an embodiment may be provided with a window to visualize the e-liquid to know whether the e-liquid is finished.

In another embodiment, the device 10 is reusable, rechargeable, and the tanks replaceable. In such an embodiment, the mouthpiece 12 of the vaporization device 10 is removable, whereby the mouthpiece 12 is entirely removable, or preferably, moveably retained on the body 14 by for instance, but not limited to, a hinge, or a hook and loop, or a tie, whereby the mouthpiece 12 can be removed so as to reveal the replaceable tanks 24. When entirely removed, the mouthpiece 12 can be removably affixed to the body, for instance, but not limited to, a snap fit via a hook and groove accommodation. The mouthpiece 12 can also be configured to act as a circuit breaker such that when the mouthpiece 12 is not secured to the body 14, the battery circuit for vaporization is open and inoperable thus providing a safety feature for the device 10, for example for travel or when not in use. When the tanks 24 are operationally secured to the battery 22 and the pen 18, the mouthpiece 12 can be closed thus allowing the device 10 to be activated through a detected pressure change effecting the sensor and the PCB thus controlling vaporization.

In a reusable embodiment, the tanks 24 can be exchangeable/replaceable whereby a tank 24 can be disconnected from the pen 18 and another affixed thereto as desired. In this way, the user can have the pleasure of combining different vaporization products produced by different e-liquids in different tanks 24. In some embodiments, the disposable tank 24 is provided with a leak proof cap, which can be removably affixed thereto in order that after removal from the pen 18 there is no leakage from the tank 24. In this way, if a tank 24 still has e-liquid in the reservoir 28, the tank can be removed and reused, or another user can access the chamber 26 with a different tank 24, without disposing of the tank 24.

Different types of pen configurations can be used in the device 10. In one embodiment of the pen 18 of the device 10, the vaporization chamber 26 is affixed to the battery 22, and therefore, a tank 24 is received by the vaporization chamber plus coil 34 which is already affixed to the battery 22. In another embodiment of the pen 18 of the device 10, the tank includes both the reservoir 28 and the vaporization chamber 26 plus coil 28, and therefore, in such an embodiment the battery 22 threadingly receives the tank 24. In such an embodiment, once the e-liquid is depleted in the tank 24, the reservoir 28 plus vaporization chamber 26 including the coil 34 can be thrown away or at least removed, preferably capped, and set aside for later reuse without any leakage into the battery and other components of the pen 18.

In an embodiment wherein the tank 24 is disposable or can be interchanged or exchanged with another tank 24, remote technology, such as for instance blue tooth technology, on each pen 18 could be provided for programming temperature and time of vaporization for different tanks 24 based on the e-liquid composition, by and through the PCB, which may include memory, and would enable the remote storage of information regarding each tank containing e-liquid preferred vaporization temperature and vaporization time. The feature in this embodiment allows more particular control and/or personalization of a vaping experience whereby a user can retrieve or store information about each e-liquid and therefore mixtures of vaporization products including ideal temperatures of vaporization. It is also contemplated that this information and control be relayed and stored via a universal serial bus ("USB") or micro-USB connection to a computer. Furthermore, a microprocessor could be used to control, maintain, and change temperatures according to different e-liquid profiles in tanks 24.

Moreover, for a non-disposable embodiment whereby the battery can be recharged and the tanks 24 replaced/exchanged, it could be beneficial to monitor the temperature of the coil 32 in order to reach and maintain the temperature of the coil 32 and thus vaporize the desired components of the e-liquid. Therefore, a temperature sensor for reading and recording the temperature of the coil, temperature in the vaporization chamber, the temperature of the vaporization product, and/or the temperature of the e-liquid in the tank 24 could be included in the device 10. Temperature changes and recordings could also be presented in an LED screen located in the body 14 of the device 10.

In addition, a PCB of the pen 18 of the device could be configured to store temperature information and/or to relay the same to a remote storage through blue tooth or remote technology. In this way, the temperature of the coil 32 of the device could be more closely monitored and adjusted for more accurate vaporization.

Whether the device 10 itself is disposable or rechargeable/reusable, by providing a device 10 whereby tanks 24 containing different e-liquid components in the reservoirs that can be vaporized at the same time but at different temperatures, a customizable vaporization experience is obtainable by the vaporization device 10 according to a user's subjective tastes and experiences, or in the case of medical use, prescribed combinations.

Figure 6:
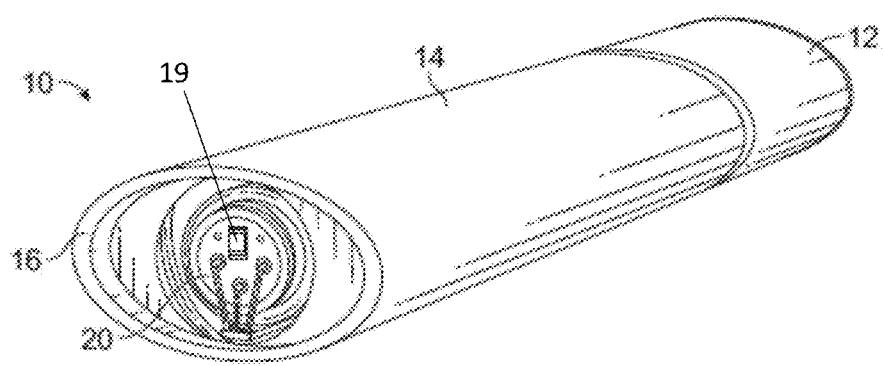
FIG. 6 illustrates an embodiment of the ventilated end of the device in accordance with the principles of the present invention.

In another embodiment, illustrated in FIG. 6, the ventilated end 16 has a single PCB and sensor 20 whereby the plurality of pens 18 housed in the body 14 are controlled by the single PCB and sensor 20, and preferably a microprocessor which can control the temperature of each of the different pens 18 so that an appropriate vaporization temperature can be accommodated by each coil 34 for each tank 24 containing in its reservoir 28 a unique e-liquid. In an embodiment whereby a plurality of pens 18 is controlled by a single PCB and sensor, different tanks 24 which contain an e-liquids of different viscosity than another tank's 24 e-liquid, and which are not combinable in a single tank 24, can still be vaporized at the same time.

Figure 9:
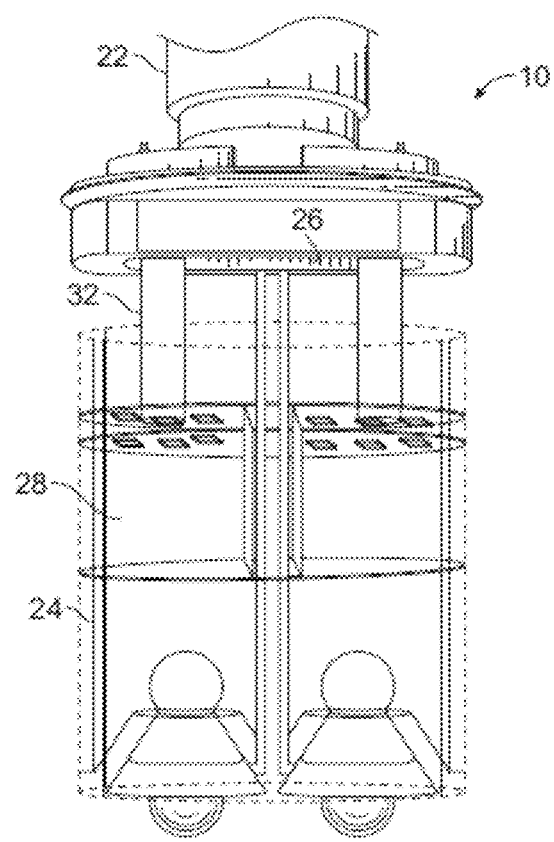
FIG. 9 illustrates an embodiment of a plurality reservoir tank being assembled onto a batter of a pen of the device in accordance with the principles of the present invention.

In yet another embodiment, as in FIG. 9 is illustrated a tank 24 being assembled onto a pen 18, whereby the tank 24 has a plurality of reservoirs 28 each for housing a different e-liquid. Although different e-liquids are provided in the tank 24, they are operationally connected to a single vaporization chamber 26. Though the advantage of mixing during vaporization is present in this embodiment, components of the e-liquid combination in the vaporization chamber 26 are vaporized all together at the same temperature. This embodiment also accommodates e-liquid which is not easily mixed due to the varying percentages of PG, VG, water and components, effecting viscosity. This embodiment also shows a dual wick 32 which allows for the delivery of e-liquid from each of the reservoirs 28 of the tank 24 to be delivered to the vaporization chamber 26 for vaporization at the same time and temperature. The battery 22 is also shown as pertaining to a single pen 18.

Figure 7:
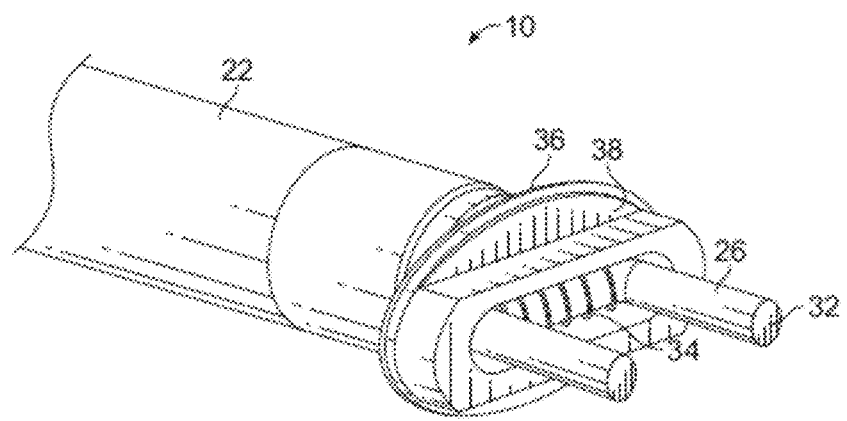
FIG. 7 illustrates an embodiment of the wick, coil and battery of the device in accordance with the principles of the present invention.

FIG. 7 illustrates a coil 34 of the device 10. In this embodiment, the dual wick 32 and coil 34 in the chamber 26 are visible. Also illustrated is a lip or O-ring 36 forming a lip to securely capture a corresponding groove on the plurality reservoir tank 30. In this way, the e-liquid in the tank 24 is less likely to be spilled because the tank 24 is secured on the wick body 38, and any jarring of the device 10 can reduce the chance of e-liquid leaking from the tank 24. In another configuration, the lip 36 can be on the tank 24 while the groove can be formed on the wick body 38. As described above, the coil 34 and vaporization chamber 26 can be contained within a disposable tank 24 whereby the tank 24 is threadingly received by the battery 22, or the coil 34 and the vaporization chamber 26 can be affixed to the battery 22 which is configured to threadingly receive a disposable tank 24 containing the e-liquid.

Figure 8:
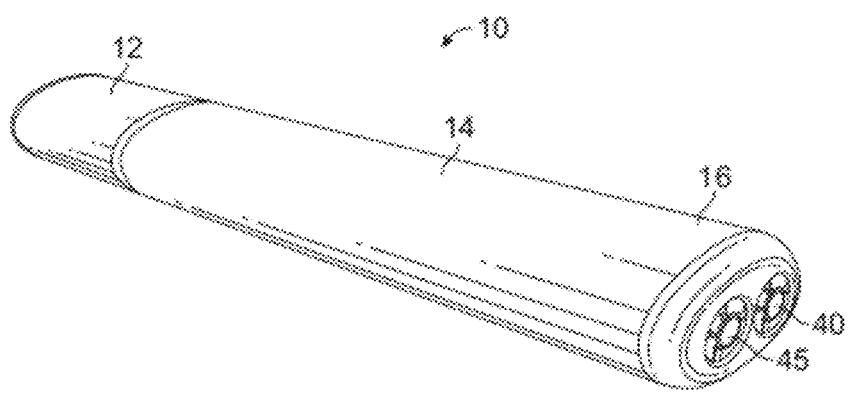
FIG. 8 illustrates an embodiment of the ventilated end showing a vortex tip of the device in accordance with the principles of the present invention.

FIG. 8 illustrates yet another embodiment of the device 10 whereby in the ventilated end 16 there is a vortex tip 40 for better air mixing through the air passage extending from the end 16 through the mouthpiece 12. In this particular embodiment, the body 14 is adjacent to and contiguous with the end 16 and is created as a single piece design. The body 14, and in this embodiment, the end 16, can be made of any material with heat dissipating properties including, for instance, but not limited to, aluminum and stainless steel, and also heat isolating materials that can reduce battery usage, provide heat dissipation properties, while at the same time isolate from the heat inside, such as for instance, but not limited to, plastics, or a combination of materials with heat dissipating and heat isolation properties. Moreover, for embodiments that have rechargeable batteries and disposable tanks, it is also contemplated that for the convenience of the user, a plurality of windows be provided in the body 14 in order to visualize the amount of e-liquid remaining in the plurality of tanks 24.

Figure 10:
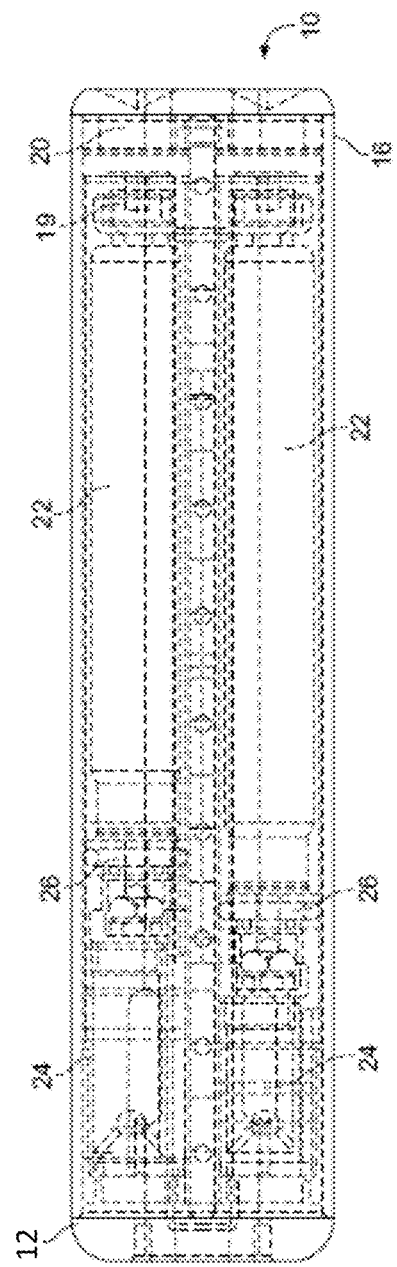
FIG. 10 illustrates a cross-section of an embodiment of the device from the mouthpiece to the ventilated end in accordance with the principles of the present invention.
Figure 11:
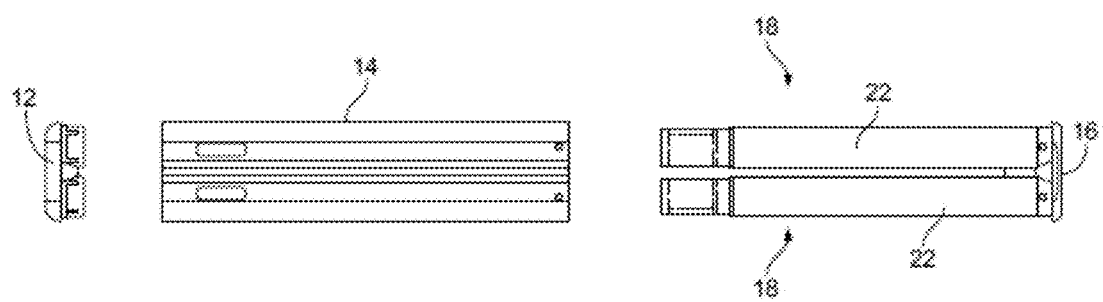
FIG. 11 illustrates an exploded view of an embodiment of the device in accordance with the principles of the present invention.

FIG. 10 illustrates a cross-section of an embodiment of the vaporization device 10 in which there are two batteries 22, one for each of the pens 18, and the batteries 22 are different sizes. As discussed before this is possible and is useful in embodiments where the e-liquid in the different tanks 24 is different and thus may require different voltages and different coils, leading to a need for different sized batteries to most effectively vaporize the e-liquid in both tanks at the same time over multiple vaporization events. In addition, it is optimum to also provide a coil 34 appropriate for vaporization of a particular e-liquid, for example a dual coil could be used for maximum vapor and a single coil for lower temperatures for a different e-liquid. Moreover, FIG. 11 illustrates an embodiment of the vaporization device 10 in an exploded view whereby it can be seen that the mouthpiece 12 is removable from the body 14 and so are the pens 18, potentially to change them or recharge them.

The battery 22 of the device 10 can be rechargeable, can be recharged/charged via induction charging, and/or can be charged by a wall electrical outlet, and/or by accommodating a USB to a computer to recharge/charge. In the case of a rechargeable embodiment of the device 10, it is possible for a rechargeable device 10 to be provided with LED lights such that a pattern for charging is detected on the body 14 or the end 16. For example, but not limited to, a pattern whereby lights flash in a pattern when the vaporization device 10 is being charged, and a different pattern when finished.

Figure 12:
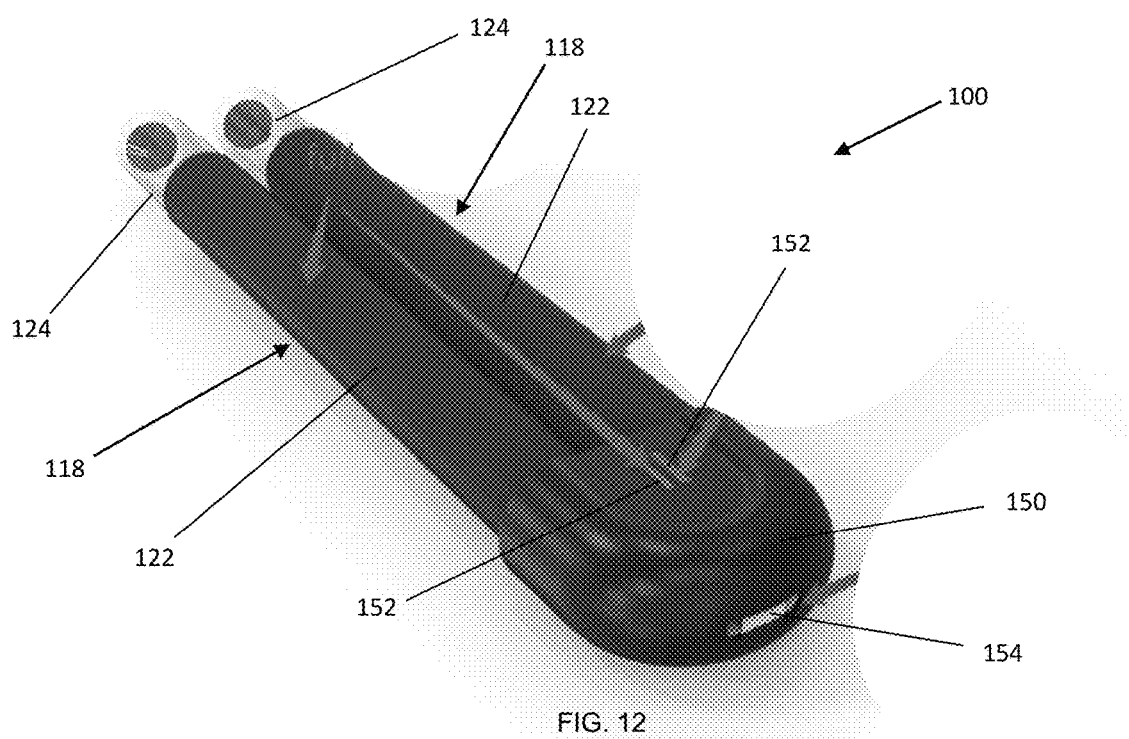
FIG. 12 illustrates a first embodiment of a charger assembled onto batteries of a rechargeable vaporization device in accordance with the principles of the present invention.
Figure 13:
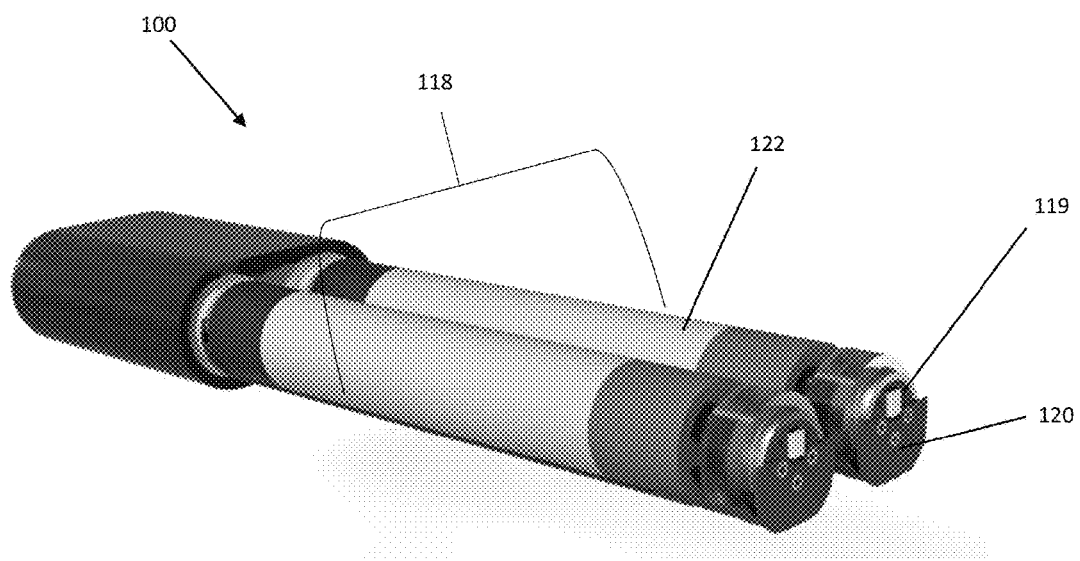
FIG. 13 illustrates internal components of an embodiment of a rechargeable vaporization device in accordance with the principles of the present invention.

Referring to FIG. 12, in an embodiment of a rechargeable vaporization device 100, pens 118 each have a tank 124 disposed at a first end of the pen 118. At least two such pens 118 would be housed within a body (see e.g., body 14 of FIGS. 2 and 3) of the rechargeable vaporization device 100. In one exemplary embodiment, the body 14 includes at least one rechargeable battery 22, 122.

Referring to FIG. 6, in one embodiment, a printed circuit board (PCB) 19 is operatively connected to the at least one rechargeable battery 22. In other embodiments, the body 14 includes a rechargeable battery 22, 122 operatively connected to each pen 118. In some of those embodiments having a rechargeable battery 22, 122 operatively connected to each pen 118, a single PCB 19, 119 is operatively connected to all of the batteries 22, 122. In other embodiments, each of the pens 118 comprises a printed circuit board (PCB) 119 operatively connected to a rechargeable battery 122. Each PCB 19, 119 is further operatively connected to a sensor 120 and a coil disposed within each of a plurality of vaporization chambers (see, e.g., coil 34 disposed within vaporization chamber 26 as illustrated in FIG. 7).

Referring again to FIG. 12, one or more batteries 122 can be disposed within a charger 150, 156 at an end of the one or more batteries 122 opposite the tanks 124. When the one or more batteries 122 are so disposed within the charger 150, 156, a second PCB (not shown) disposed within the charger 150, 156 is operatively connected to the one or more batteries 122 and/or the one or more PCBs 19 that are operatively connected to the one or more batteries 122. For example, in an exemplary embodiment where a single PCB 19 is operably connected to a plurality of batteries 122, the second PCB (not shown) is operatively connected to the plurality of batteries 122 and/or to the single PCB 19. In another exemplary embodiment where each battery 122 is operably connected to a PCB 19, the second PCB (not shown) is operably connected to each battery and/or to each PCB 19. For any of the embodiments described hereinabove or for other configurations of one or more batteries operatively connected to one or more PCBs 19, the second PCB (not shown) within the charger 150, 156 determines power requirements of the one or more batteries 122 and charges the one or more batteries 122 according to the power requirements.

Figure 14:
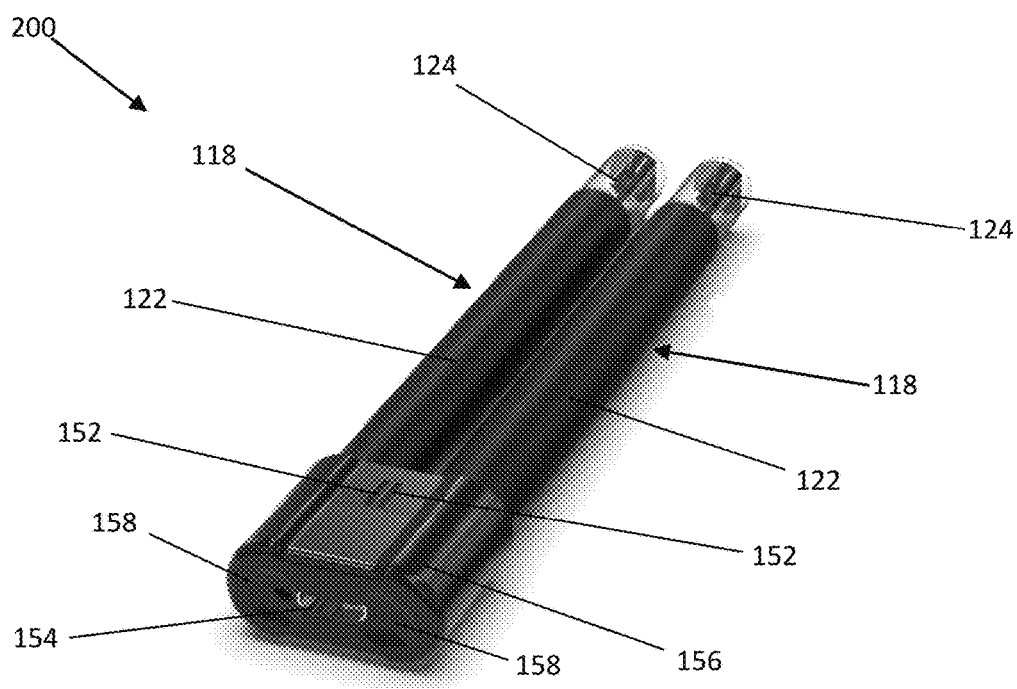
FIG. 14 illustrates a second embodiment of a charger assembled onto batteries of a rechargeable vaporization device in accordance with the principles of the present invention.
Figure 15:
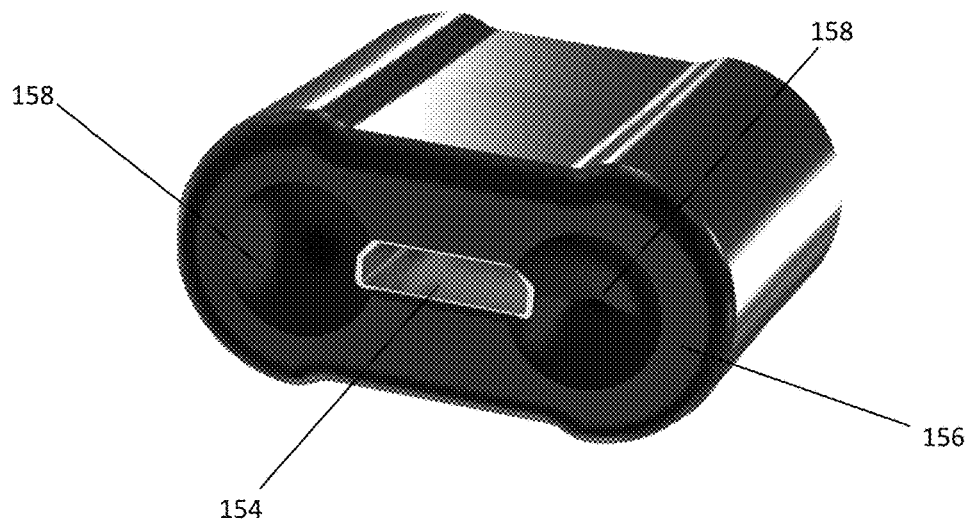
FIG. 15 illustrates the second embodiment of the charger disassembled from batteries of a rechargeable vaporization device in accordance with the principles of the present invention.

In another embodiment of a rechargeable vaporization device 200, as illustrated in FIGS. 14 and 15, the charger 156 is removably attached to the batteries 122. Such removable attachment allows the batteries 122 to be replaced if necessary. FIG. 14 illustrates the removably attachable charger 156 attached to the batteries 122 and FIG. 15 illustrates the removably attachable charger 156 detached from the batteries 122.

Referring generally to FIGS. 12-15, in some embodiments the charger 150, 156 comprises a light 152 visible through a surface thereof and associated with the charge state of each battery 122. The lights 152 can be triggered by the second PCB to flash in predetermined patterns or to illuminate in various colors descriptive of the charge state for each battery 122. In one embodiment, each light 152 is illuminated a first color, e.g., red, if the battery charge is below a first percentage of total charge, e.g., about 30%. In this embodiment each light 152 is illuminated a second color, e.g., green, if the battery charge is between the first percentage of total charge and a second percentage of total charge, e.g., 70%, and further, each light 152 is illuminated a third color, e.g., blue, if the battery charge is above the second percentage of total charge. The second PCB also includes circuitry that prevents overcharging of the batteries.

Power is provided to the charger 150, 156 through an interface 154 operatively connected to the second PCB. In some embodiments the interface 154 can be a plugin port such as a USB port, a micro-USB port, or other type of plugin port as known in the art, as illustrated in FIGS. 12, 14, and 15. Another embodiment utilizes an inductive charging receiver (not shown) disposed within the charger 150, 156 to allow for wireless power input to the charger 150, 156. Those embodiments utilizing a plugin port for the interface 154 have the plugin port preferably disposed on an end of the charger 150, 156 as illustrated in FIGS. 12, 14, and 15, though the position of the plugin port is not limited to this position and could be disposed anywhere on the charger 150, 156.

Positioning the interface 154 on the end of the charger 150, 156 makes it generally easy to plug a male end of a plugin port into the interface 154, and in particular allows the charger 150, 156 to be placed vertically on a charging dock (not shown) with the interface 154 facing down. As best illustrated in FIGS. 14 and 15, in some embodiments the charger 150, 156 includes magnetic connectors 158 that allow for secure attachment of the charger 150, 156 to the charging dock having the male end of a plugin port. For those embodiments having an inductive charging receiver as the interface 154, the magnetic connectors allow for secure attachment of the charger 150, 156 to the inductive charging plate. Regardless of the type of interface 154, power input to the charger 150, 156 through the interface 154 is monitored by circuitry within the second PCB to protect the second PCB from over voltage or a short circuit received through the interface 154.

INDUSTRIAL APPLICABILITY

The charger for a vaporization device determines power requirements of a vaporization device battery (or batteries) and charges the battery according to the power requirement. The charger visually indicates the charge level of the battery and includes circuitry to prevent overcharging. The charger accepts power via a plug-in interface or via an inductive charging interface. The charger can be attached to the battery (or batteries) or removable therefrom.

Numerous modifications to the present invention will be apparent to those skilled in the art in view of the foregoing description. It is not desired to limit the invention to the exact construction and operation shown and described, and accordingly, all suitable modifications and equivalents may be resorted to, falling within the scope of the invention. Accordingly, this description is to be construed as illustrative only of the principles of the invention and is presented for the purpose of enabling those skilled in the art to make and use the invention and to teach the best mode of carrying out same. The exclusive rights to all modifications which come within the scope of the appended claims are reserved. All patents, patent publications and applications, and other references cited herein are incorporated by reference herein in their entirety.

I claim:
1. A rechargeable vaporization device comprising:
   a body configured to house at least two pens, and a first printed circuit board (PCB) operatively connected to a rechargeable battery in a cavity inside the body;
   each pen comprising a sensor, and a coil disposed within each of a plurality of vaporization chambers; wherein
   a charger is attached to an end of the battery and comprises a second PCB operatively connected to the battery, where the second PCB determines power requirements of the battery and charges the battery according to the power requirements.

2. The rechargeable vaporization device of claim 1, wherein each pen comprises a rechargeable battery, where the second PCB determines power requirements of the batteries and charges the batteries according to the power requirements.

3. The rechargeable vaporization device of claim 2, wherein each pen comprises a first PCB operatively connected to a rechargeable battery, where the second PCB determines power requirements of the batteries and charges the batteries according to the power requirements.

4. The rechargeable vaporization device of claim 1, where the charger comprises a light visible in a surface thereof associated with the rechargeable battery, and where the light is illuminated a first color if the battery charge is below a first percentage of total charge, illuminated a second color if the battery charge is between the first percentage of total charge and a second percentage of total charge, and illuminated a third color if the battery charge is above the second percentage of total charge.

5. The rechargeable vaporization device of claim 1, where the second PCB includes circuitry that prevents overcharging of the battery.

6. The rechargeable vaporization device of claim 1, where the charger accepts power via an interface selected from the group including a USB port, a micro-USB port, and an inductive charging receiver, where the interface is operationally connected to the second PCB.

7. The rechargeable vaporization device of claim 6, wherein the charger comprises magnetic connectors that attach to a charging dock or an inductive charging plate.

8. The rechargeable vaporization device of claim 6, where the second PCB further comprises circuitry that monitors power input through the interface to protect the second PCB from over voltage or a short circuit received through the interface.

9. The rechargeable vaporization device of claim 6, wherein the charger is removably attached to the battery.

10. A rechargeable vaporization device comprising:
a body configured to house at least two pens, and a first printed circuit board (PCB) operatively connected to a rechargeable battery in a cavity inside the body;
each pen comprising a sensor, and a coil disposed within each of a plurality of vaporization chambers; wherein
a plurality of tanks each comprises a reservoir configured to contain an e-liquid, where each reservoir is operatively connected to one of the plurality of vaporization chambers; and wherein
a charger is attached to an end of the battery and comprises a second PCB operatively connected to the battery, where the second PCB determines power requirements of the battery and charges the battery according to the power requirements.

11. The rechargeable vaporization device of claim 10, wherein each pen comprises a rechargeable battery, where the second PCB determines power requirements of the batteries and charges the batteries according to the power requirements.

12. The rechargeable vaporization device of claim 11, wherein each pen comprises a first PCB operatively connected to a rechargeable battery, where the second PCB determines power requirements of the batteries and charges the batteries according to the power requirements.

13. The rechargeable vaporization device of claim 10, where the charger comprises a light visible in a surface thereof associated with the battery, and where the light is illuminated a first color if the battery charge is below a first percentage of total charge, illuminated a second color if the battery charge is between the first percentage of total charge and a second percentage of total charge, and illuminated a third color if the battery charge is above the second percentage of total charge.

14. The rechargeable vaporization device of claim 10, where the second PCB includes circuitry that prevents overcharging of the battery.

15. The rechargeable vaporization device of claim 10, where the charger accepts power via an interface selected from the group including a USB port, a micro-USB port, and an inductive charging receiver, where the interface is operationally connected to the second PCB.

16. The rechargeable vaporization device of claim 15, wherein the charger comprises magnetic connectors that attach to a charging dock or an inductive charging plate.

17. The rechargeable vaporization device of claim 15, where the second PCB further comprises circuitry that monitors power input through the interface to protect the second PCB from over voltage or a short circuit received through the interface.

18. The rechargeable vaporization device of claim 15, wherein the charger is removably attached to the battery.

19. The rechargeable vaporization device of claim 10, wherein the plurality of tanks is removable from each pen.

* * * * *